(12) United States Patent
Chrisman

(10) Patent No.: US 10,912,325 B2
(45) Date of Patent: Feb. 9, 2021

(54) TABLET CONTAINING CEYLON CINNAMON POWDER

(71) Applicant: Timothy Chrisman, Falls Church, VA (US)

(72) Inventor: Timothy Chrisman, Falls Church, VA (US)

(*) Notice: Subject to any disclaimer, the term of this patent is extended or adjusted under 35 U.S.C. 154(b) by 0 days.

(21) Appl. No.: 16/672,602

(22) Filed: Nov. 4, 2019

(65) Prior Publication Data
US 2020/0060320 A1    Feb. 27, 2020

(51) Int. Cl.
| | | |
|---|---|---|
| A61K 36/00 | (2006.01) |
| A23L 33/105 | (2016.01) |
| A61K 36/9066 | (2006.01) |
| A61K 36/54 | (2006.01) |
| A61K 36/76 | (2006.01) |
| A61K 36/324 | (2006.01) |
| A61K 36/9068 | (2006.01) |
| A61K 36/53 | (2006.01) |

(52) U.S. Cl.
CPC .......... *A23L 33/105* (2016.08); *A61K 36/324* (2013.01); *A61K 36/53* (2013.01); *A61K 36/54* (2013.01); *A61K 36/76* (2013.01); *A61K 36/9066* (2013.01); *A61K 36/9068* (2013.01)

(58) Field of Classification Search
CPC ...................................................... A61K 36/00
USPC ........................................................ 424/725
See application file for complete search history.

(56) References Cited

U.S. PATENT DOCUMENTS 7,678,768 B2 * 3/2010 Purpura ............... A61P 9/00
                                                         514/13.3

* cited by examiner

*Primary Examiner* — Michael V Meller

(57) ABSTRACT

The present invention relates to a tablet and a method for stabilizing and reversing the effects of age and activity related inflammation in persons over the age of 18.

1 Claim, No Drawings

TABLET CONTAINING CEYLON CINNAMON POWDER

BACKGROUND OF THE INVENTION

Field of the Invention

The present invention relates to a tablet and a method for stabilizing and reversing the effects of age and activity related inflammation in persons over the age of 18. The method includes administering a dosage three times a day of not less than 500 mg and not more than 600 mg Ceylon Cinnamon Powder, not less than 450 mg and not more than 550 mg Bromelain standardized at 2400 Gelatin Digestive Units/Gram and 3600 Milk Clot Units/Gram, not less than 450 mg and not more than 550 mg Turmeric Rhizomes Curcumin C3 Complex (also known as *Curcuma longa*) standardized to 95% Curcuminoids, not less than 400 mg and not more than 475 mg Devil's Claw Root (*Harpagophytum procumbens, Harpagophytum zeyheri*) extract standardized to 2.5-3.5% Harpagosides, not less than 200 mg and not more than 300 mg *Boswellia serrata* (resin) extract standardized to 70% Boswellic Acid, not less than 150 mg and not more than 250 mg Ginger Root SE standardized to 20% total gingerols and shogaols, not less than 75 mg and not more than 125 mg White Willow (also known as *Salix alba*) extracted at 25% Salicin, not less than 30 mg and not more than 40 mg Cayenne Pepper Extract standardized to 90,000 heat units, and not less than 8 mg and not more than 12 mg Bioperine (Black Pepper).

SUMMARY OF THE INVENTION

The invention is a formulation. The ingredients are combined into a tablet.
1) 550 mg Ceylon Cinnamon Powder.
2) 500 mg Bromelain (Standardized at 2400 Gelatin Digestive Units/Gram, 3600 Milk Clot Units/Gram).
3) 500 mg Turmeric (Rhizomes) Curcumin C3 Complex (Standardized to 95% Curcuminoids Also known as: *Curcuma longa*).
4) 435 mg Devil's Claw (Root) (Standardized to 2.5-3.5% Harpagosides, also known as: *Harpagophytum procumbens, Harpagophytum zeyheri*).
5) 250 mg *Boswellia serrata* (Resin) Extract (Standardized to 70% Boswellic Acid).
6) 200 mg Ginger Root SE (Standardized to 20% total gingerols and shogaols).
7) 100 mg White Willow (Extracted at 25% Salicin, also known as: *Salix alba*).
8) 35 mg Cayenne Pepper Extract (Standardized to 90,000 heat units).
9) 10 mg Bioperine (from Black Pepper also known as *Piper nigrum*). The tablet is to be taken three times daily preferably with a meal to help relieve the symptoms of inflammation.

The tablet is a nutritional supplement designed to combat inflammation. It combines the eight most researched anti-inflammatory natural compounds into a single supplement.

The invention claimed is:
1. A tablet or capsule consisting essentially of not less than 500 mg and not more than 600 mg Ceylon Cinnamon Powder, not less than 450 mg and not more than 550 mg Bromelain (standardized at 2400 Gelatin Digestive Units/Gram and 3600 Milk Clot Units/Gram), not less than 450 mg and not more than 550 mg Turmeric Rhizomes Curcumin C3 Complex standardized to 95% Curcuminoids, not less than 400 mg and not more than 475 mg Devil's Claw Root extract standardized to 2.5-3.5% Harpagosides, not less than 200 mg and not more than 300 mg *Boswellia serrata* resin extract standardized to 70% Bosweilic Acid, not less than 150 mg and not more than 250 mg Ginger Root standardized to 20% total gingerols and shogaols, not less than 75 mg and not more than 125 mg White Willow extracted at 25% Salicin, not less than 30 mg and not more than 40 mg Cayenne Pepper Extract standardized to 90,000 heat units, and not less than 8 mg and not more than 12 mg Bioperine Black Pepper.

* * * * *